United States Patent [19]
Mori et al.

[11] Patent Number: 5,633,275
[45] Date of Patent: May 27, 1997

[54] PHOTOCHEMOTHERAPEUTICAL OBSTRUCTION OF NEWLY-FORMED BLOOD VESSELS

[75] Inventors: Keisuke Mori; Masataka Ohta; Shigeru Mori; Shin Yoneya; Naoki Hayashi; Masaru Sonoda, all of Saitama-ken, Japan

[73] Assignee: Meiji Seika Kaisha, Ltd., Tokyo, Japan

[21] Appl. No.: 616,177

[22] Filed: Mar. 15, 1996

[30] Foreign Application Priority Data

Sep. 6, 1995 [JP] Japan .................... 7-228760

[51] Int. Cl.$^6$ .................... A61K 31/40
[52] U.S. Cl. .................... 514/410
[58] Field of Search .................... 514/410

[56] References Cited

U.S. PATENT DOCUMENTS

| | | | |
|---|---|---|---|
| 4,675,338 | 6/1987 | Bommer et al. | 514/410 |
| 4,997,639 | 3/1991 | Aizawa et al. | 424/9 |
| 5,308,861 | 5/1994 | Aizawa et al. | 514/410 |

*Primary Examiner*—Raymond Henley, III
*Attorney, Agent, or Firm*—Larson & Taylor

[57] ABSTRACT

A photosensitive tetrapyrrole derivative having formula (I)

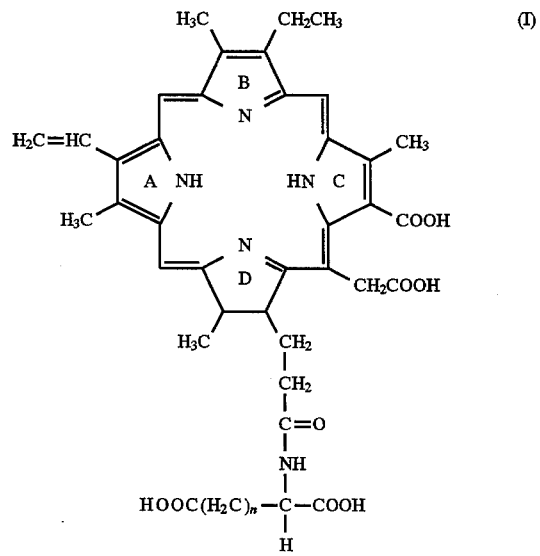

where n stands for 1 or 2 or a pharmaceutically acceptable salt thereof is useful as an effective ingredient in an obstruent composition for photochemotherapeutically obstructing neovascular vessels. The photosensitive tetrapyrroles of the formula (I) may be administered in a photochemotherapeutic method for obstructing neovascular vessels, particularly choroidal and retinal neovascularizations.

2 Claims, No Drawings

PHOTOCHEMOTHERAPEUTICAL OBSTRUCTION OF NEWLY-FORMED BLOOD VESSELS

FIELD OF THE INVENTION

The present invention relates to an obstruent composition for use in photochemotherapeutical obstruction or occlusion of newly-formed or neovascular blood vessels as formed in a patient. The present invention also relates to a method for photochemotherapeutically obstructing neovascular vessels as formed in a patient having the neovascular vessels in eyes, cutaneous tissue or visceral tissue.

BACKGROUND OF THE INVENTION

The photochemotherapeutical method means such a chemotherapeutical method which makes use of a photosensitive substance capable of displaying a therapeutic action or medical action for the first time only when said substance is elicited photochemically by being irradiated with light, for example, ultraviolet rays or a beam of laser light, and in which, after the administration of said photosensitive substance, either such part or parts of the tissues of a living body of the patient where the photosensitive substance as administered has been presented and accumulated, or a flow of blood as formed by extracorporeal circulation of the blood containing said photosensitive substance is exposed to irradiation with light or is subjected to any other measure so that the photosensitive substance is elicited photochemically to display its therapeutic or medical action.

Upon the beginning of the development of the photochemotherapy, the photosensitive substances of a first generation, of which a representative is photofrin, were used in the therapeutic treatment of tumors or cancerous tissues. From the viewpoint of clinical application, however, the photosensitvive substance of the first generation are accompanied by their drawback that they are very much slowly metabolized in vivo.

Known photochemotherapeutic methods for treatment of tumor or cancer include such a method wherein such a photosensitiser having no anti-neoplastic activity by itself but having an affinity for tumor or cancer is administered to a patient and the photosensitiser is allowed to concentrate in the tissue of tumor or cancer, followed by irradiating the tumor or cancerous tissue with a laser light so that the tumor or cancerous tissue is treated therapeutically. The photosensitiser used in the above-mentioned method can exert such a mechanism that the photosensitiser, when exposed to the laser light, absorbs the photo-energy of the laser and becomes elicited photochemically and the energy of the elicited photosensitiser can then elicits the oxygen components present in the tumor or cancer cells to produce activated oxygen, and that the activated oxygen so produced can give damages to the tumor or cancer cells so as to cause necrosis of the tumor or cancer tissue.

For instance, in Japanese patent publication No. 88902/94 and No. 89000/94 as well as European patent publication No. 168832-B1 and U.S. Pat. No. 4,675,338, there is disclosed that diagnosis and therapeutic treatment of tumor or cancereous tissues is conducted with using as a photochemotherapeutic agent such fluorescent tetrapyrrole derivatives or salts thereof which are prepared by condensing an aminodicarboxylic acid of 4 to 10 carbon atoms, for example, aspartic acid or glutamic acid, via one or more amido linkages with at least one carboxyl group of certain tetrapyrrole compounds bearing a plurality of carboxyl group(s) and side chain(s) of carboxylic acids. There is also disclosed that the aforesaid fluorescent tetrapyrrole derivative, which has concentrated and been accumulated in the tissue of tumor or cancer, can be elicited photochemically by being irradiated with intense light, for example, a laser beam and thereby becomes able to exert its effects of killing the tumor or cancer cells.

Further, it is known that the formation of neovascular blood vessels, namely neovascularization occurs in various ocular tissues in the eyes due to certain pathogenic causes.

Neovascularization of any ocular tissue causes serious visual disturbance. Particularly, choroidal neovascularization which takes place accompanying with age-related macular degeneration is now becoming a primary cause for acquired blindness. In age-related macular degeneration, choroidal neovascularization causes subretinal hemorrhage, exudates and fibrosis, leading to severe visual loss.

Laser photocoagulation has heretofore been used for the therapeutic treatment of choroidal (ocular) neovascularization but is not a perfect method, because it damages overlying sensory retina by propagating heat. Compared with the above method, photochemotherapy using a laser beam is expected to provide a satisfactory therapeutic method for neovascularization, if the neovascular, ocular blood vessels can be selectively targeted by the photochemotherapy with the laser beam.

Sometimes, it is also desired to selectively obstruct or occlude newly-formed vessels other than the above-described ocular Ones, for example, those formed in skin tissue or visceral tissue due to a certain pathogenic cause.

An object of the present invention is to provide a new obstruent composition for use in obstructing or occluding photochemotherapeutically and selectively a part or all or some parts of newly-formed vessels formed in the various ocular tissues, as well as newly-formed vessels formed in other tissues in vivo. The other object of the present invention is provide a therapeutic method for photochemotherapeutically obstructing neovascular blood vessels as formed in a patient having the neovascular blood vessels. Another objects of the present invention will be clear from the following descriptions.

DETAILED DESCRIPTION OF THE INVENTION

In order to achieve the above-mentioned objects of the present invention, the present inventors have made investigations for seeking a photochemotherapeutic agent which is useful and suitable to obstruct or occlude various kinds of neovascular vessels, especially choroidal or retinal neovascularization. As a result of the investigations, the present inventors have now found that when patients having the neovascular vessels are administered with a photosensitive substance, mono-L-aspartly-chlorin e6 tetra-sodium salt (hereinafter abbreviated as "NPe6") which is now employed and tested in a clinical application of a photochemotherapeutic treatment of malignant tumors and is known to be quickly uptaken into and excreted from the human and animal body, NPe6 can concentrate into and be accumulated well in the active lesions of the neovascular tissues, and that NPe6 present in the neovascular vessels can be elicited by irradiation with a laser beam at a wavelength of 664 nm and the elicited NPe6 is able to generate the activated oxygen and thereby to cause necrosis of the vascular endothelial cells and occlusion of choroidal neovascularization.

Further, the present inventors have found that not only the above-mentioned NPe6 substance but also a tetrapyrrole derivative represented collectively by a general formula (I)

given below, including the NPe6 substance, are utilizable effectively and highly safely as such an obstruent for obstructing or clogging the newly-formed vessels, which can be activated by irradiation with a light when it is used in a photochemotherapy. It has also been found that the tetrapyrrole derivative having the general formula (I) given below are especially useful and effective with a high safety to obstruct the choroidal neovascularization as well as the retinal neovascularization. On the basis of these findings, the present inventors have completed the present invention.

In a first aspect of the present invention, therefore, there is provided an obstruent composition for photochemotherapeutically obstructing the neovascularization, which comprises as the effective ingredient a compound represented by the formula(I):

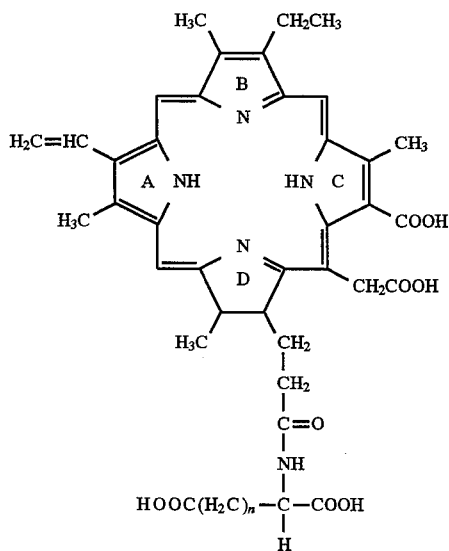

where n stands for an integer of 1 or 2, or a pharmaceutically acceptable salt thereof; and a pharmaceutically acceptable carrier for the effective ingredient.

The tetrapyrrole derivative of the general formula (1), which is used as the effective ingredient in the obstruent composition according to the first aspect of the present invention, may preferably be its stereoisomer having a steric configuration shown below and represented by the following general formula (I'):

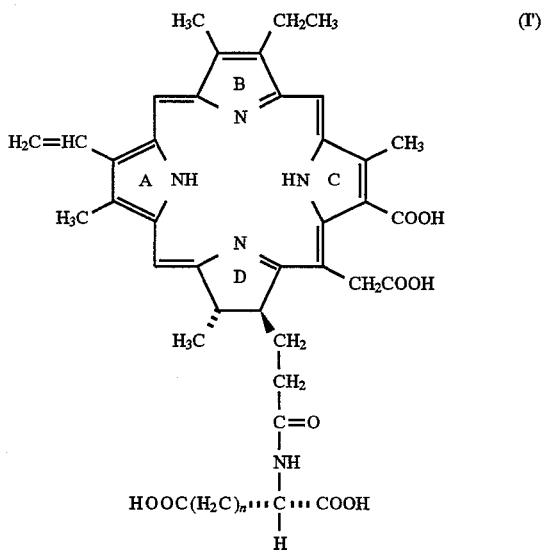

where n stands for an integer of 1 or 2.

Among the compounds of the general formula (I') shown above, the compound of the formula (I') where n is 1 is such compound wherein L-aspartic acid is combined via an amido linkage with the side chain group —CH$_2$CH$_2$COOH of the tetrapyrrole ring shown in the above formula (I'). This particular compound is mono-L-aspartyl-chlorin e6. This mono-L-aspartyl-chlorin e6 may preferably be in the form of its tetra-sodium salt (abbreviated as "NPe6") at the four carboxyl groups of the compound.

Among the compounds of the general formula (I') shown above, the compound of the formula (I') where n is 2 is such compound wherein L-glutamic acid, in stead of said L-aspartic acid, is combined via the amido linkage of the side chain group —CH$_2$CH$_2$COOH of the tetrapyrrole ring shown in the formula (I'). This compound is mono-L-glutamyl-chlorin e6.

While, the compound of the general formula (I) or formula (I') generally may form a salt thereof by reaction with a base. Examples of such salt with the base may include the sodium, potassium, calcium, magnesium, ammonium, triethylammonium, trimethylammonium, morpholine and piperidine salts.

The compound of the above formula (I), particularly the compound of the above formula (I') is able to concentrate into and be accumulated well in the blood vessels in the eyes after the administration of said compound. And, the compound accumulated in the ocular blood vessels is able to obstruct the choroidal or retinal neovascularization when the compound is activated by the action of a laser beam irradiating a limited region of the neovascular tissues. In particular, NPe6 is a photosensitivity-improver consisting essentially of a single compound wherein one molecule of L-aspartic acid is combined via the amido linkage with the side chain group —CH$_2$CH$_2$COOH attached to the chlorin ring which is formed by the reduction of a single one double-bond of the D ring of the tetrapyrrole nucleus. NPe6 is characterized by that this specific compound can absorb well a light having a wavelength of 664 nm. Besides, NPe6 has a high metabolic speed which is at least 10 times faster than that of the aforesaid "photofrin", and at the end of 10 hours from the administration of NPe6, the level of NPe6 in the blood plasma can reach a level as high as 1/500 of the dosage of administration of NPe6.

It has also been found that NPe6 is further characterised by that NPe6 has a nature of exhibiting affinity to the serum albumin, that NPe6 is of a low liposolubility and thus is hard to penetrate and diffuse into the healthy normal tissues having the barrier in vivo, and that NPe6 is able to transfer into the in vivo cells not by the diffusion of the NPe6 molecules but by the phagocytosis and/or pinocytosis of the NPe6 molecules. The above-mentioned characteristic properties of NPe6 reveal that NPe6 is a photosensitive agent which can advantageously be utilized to photochemotherapeutically obstruct various ocular neovascularizations.

Incidentally, the tetrapyrrole derivative of the general formula (I) shown above and the processes of producing it are disclosed in the aforesaid Japanese patent publication No. 88902/94 and No. 89000/94 as well as in the European patent application publication No. 168832-B1 specification and U.S. Pat. No. 4,675,338.

The obstruent composition for obstructing the newly-formed vessels according to the first aspect of the present invention is useful to be used in a photochemotherapeutic treatment of a variety of ocular diseases. The composition of the present invention is particularly effective to therapeutically treat various diseases caused by the neovascularization occurring in the choroid, for example, age-related macular degeneration, and the neovascularization occurring in the retina, for example, proliferative diabetic retinopathy, and so on.

The obstruent composition according to the first aspect of the present invention, or the compound of the formular (I) or the formula (I') itself which is incorporated as the effective ingredient in said obstruent composition, may be administered to a patient either orally or parenterally by intravenous or intramuscular injection, or percutaneously. For instance, the obstruent composition of the present invention may be formulated into such a preparation which contains the compound of the formula (I) or (I') in the form of its sodium salt and has been lyophilized in the form of a sterile powder containing no pyrogen. A preferred preparation of the composition is an injectable and isotonic aqueous solution containing the compound of the formula (I) or (I'). When the compound of the formula (I) or (I') has been administered to a patient, it is possible that a laser light is irradiated to the neovascular vessels formed in the affected part or parts of the patient at an appropriate time between the time immediately after the administration and the time of up to 6 hours from the administration of said compound.

In the composition for oral administration, the compound of the formula (I) as the effective ingredient may be admixed with a pharmaceutically acceptable solid or liquid carrier or vehicle. The orally admintstrable composition may be formulated into intestinally adsorbable forms, such as tablets, buccal preparations, troches, capsules, sweetened tinctures, suspensions, syrups, wafers, or the like.

It is preferable that the composition so prepared contains the compound of the formula (I) or (I') as the effective ingredient in an amount of at least 0.1% by weight on the weight basis of the composition. The proportion of the compound of the formula (I) or (I') in the composition naturally varies depending on the form of the preparation as formulated of the composition. A preferred proportion of the effective compound of the formula (I) or (I') may be in a range of from about 2% to 60% by weight of each dosage unit of the composition. It is desirable that each dosage unit of the orally administrable composition as formulated contains about 50 to 300 mg of the compound of the formula (I) or (I') as the effective ingredient.

Preferred examples of the preparation form for injection include an aqueous sterile solution or dispersion and a sterile injectable lyophilized preparations. Illustrative carriers useful therefor include water, ethanol, and polyols such as glycerol, propylene glycol and liquid polyethylene glycol, as well as desired mixed solvents thereof. In addition, a solvent or dispersing medium containing a vegetable oil can also be used. The liquid-form preparations can be maintained appropriately flowable by adding a viscosity modifier such as lecithin. In the case of a dispersion-type preparation, its appropriate flowability can be maintained by controlling the effective ingredient compound to a desired particle size or by adding a surfactant. In many cases, it is preferred to add an isotonic agent such as sugar or sodium chloride. The injectable composition can contain an added agent capable of sustaining the absorption of the effective ingredient compound, such as aluminum monostearate or gelatin.

The dosage of the compound of the formula (I) contained in the obstruent composition according to the present invention may vary depending on the purpose of the treatment, the severity of the symptoms and the like. In general, a dose of 0.2 to 10 mg of the effective compound may be administered once a day to an adult.

Examples of the irradiation source for a laser beam, which is for use in the therapeutic treatment after the administration of the obstruent composition, include a powerful continuous laser beam sources equipped with optical filters, excited pigments and other laser-beam feeding systems. Among them, desired is an irradiation source which can generate a laser beam at a full output power of at least 500 mW to give a radiation intensity of 10 to 100 mW/cm$^2$. Some of commercially-available laser generators can satisfy the above-mentioned standards for the laser generation.

When the acute toxicity of NPe6 was tested by intravenous injection to CD-1 mice (male), it has been found that NPe6 exhibits an LD$_{50}$ value of 164 mg/kg. Prom further photo-toxicity tests with NPe6, it has been found that NPe6 is a highly safe compound which does not involve adverse side reactions such as erythema and edema.

As described in the above, the tetrapyrrole. derivative of the formula (I) or (I') shown hereinbefore is evidently useful in the photochemotherapy to abstruct or clog the neovascular vessels as formed in a patient having the neevascular vessels produced due to certain pathogenic causes.

In a second aspect of the present invention, therefore, there is provided a method for photochemotherapeutically obstructing neovascularization or neovascular blood vessels as formed in a patient having the neovascular blood vessels, which comprises administering orally or parenterally to the patient an amount of compound of the formula (I):

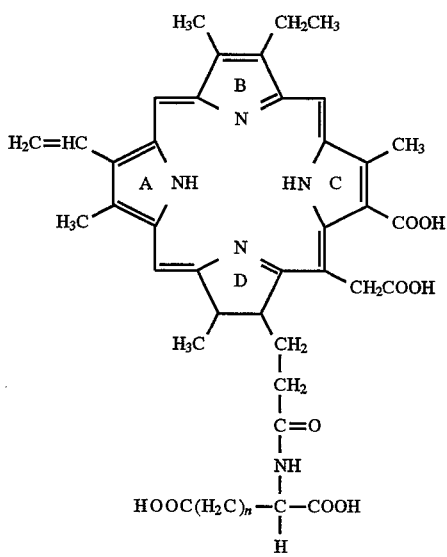

where n stands for an integer of 1 or 2, or a pharmaceutically acceptable salt thereof, allowing said compound administered to accumulate in the neovascular vessels to be obstructed after the administeration of said compound to the patient, irradiating a part or all or some parts of the neovascular vessels to be obstructed, with a laser beam until the compound accumulated in the neovascular vessels has been elicited photochemically, terminating the irradiation of the laser beam, and then allowing the laser beam-irradiated part or parts of the neovascular vessels to be obstructed.

The therapeutic method according to the second aspect of the present invention is especially useful to be applied to photochemotherapeutic obstruction of the choroidal or rotanal neovascularization formed in the patient. The compound of the formula (I) used in the method of the second aspect of the present invention may preferably be a compound of the formula (I') shown hereinbefore and may be administered in a dosage as explained for the obstruent composition according to the first aspect of the present invention hereinbefore.

The present invention is now illustrated with reference to the following Examples, to which the present invention is limited in no way.

TEST EXAMPLE 1

Injectable aqueous solutions containing NPe6 dissolved in a physiological saline were intravenously injected into seven eyes of four, normal pigmented rabbits, respectively at doses of NPe6 of 25 mg/kg, 50 mg/kg and 100 mg/kg. Immediately after the intravenous injection or one hour after the intravenous injection of the NPe6 solution, predetermined regions of the blood vessels in the seven eyes under test were irradiated with a beam of laser light having a wavelength of 664 nm (as emitted from a semiconductor generator for laser, manufactured by Matsushita Electric works Ltd., Japan) for 9 seconds or 90 seconds, while the laser beam having a power of 10 mW was injected to irradiate several spots each of 500 μn in its diameter within the blood vessels to be irradiated. The predetermined regions (that is, said spots) of the blood vessels to be irradiated with the laser beam had been marked preliminarily by photocoagulation by means of an argon laser beam. Immediately after the irradiation with the laser at 664 nm, as well as one week after the irradiation and one month after the irradiation with the laser at 664 nm, the fundus of the eyes under test was examined by fluorescein angiography. In selected cases, fundus treated with NPe6 were further examined histologically.

(1) With the treated eyes which had been subjected to the irradiation with the laser at 664 nm immediately after the intravenous injection of the NPe6 solution and were observed and examined by the fluoresein angiography made one week after the laser irradiation, it was found that the obstruction took place in the choroidal vessels at all the doses of NPe6 of 25, 50 and 100 mg/kg, and that the degree of the obstruction in the choroidal vessels increased with an increased doses of NPe6.

(2) Comparisons were made between the test results obtained when the intravenous injection of a dose of 25 mg/kg of NPe6 was followed immediately by the irradiation with the laser at 664 nm, and the test results obtained when the intravenous injection of a dose of 25 mg/kg of NPe6 was followed by the laser irradiation one hour after the intravenous injection of NPe6. It was then found that the extent of damages incurred in the choroidal vessels is reduced at the laser irradiation as made one hour after the intravenous injection of the NPe6 solution, than that incurred at the laser irradiation made immediately after the intravenous injection of NPe6. This likelihood could be observed commonly for all the doses of NPe6. This reveals that the level of NPe6 in the blood after the administration of NPe6 can decrease quickly during an earlier period after the administration of NPe6, and that NPe6 can be metabolized well after its administration into a human or animal body.

(3) The eye having received the intravenous injection of a dose of 25 mg/kg of NPe6 was subjected to the irradiation with the laser at 664 nm immediately after the intravenous injection of NPe6. The eye so treated was subsequently observed under light microscope at the end of 2 hours after the laser irradiation. By this observation, it was found that endothelial cells of the chorio-capillaris had been swollen and necrotized and the choriocapillaris were obstructed. In the sensory retina of the eye so treated, it was observed that there took place such partial movements of the inner and outer segments of photoreceptor cells into the subretinal space, which might be considered to be a slough of the visual cells. However, it was found that the whole structure of the sensory retina could be retained intact as a whole. From these findings, it is presumed that the associated actions of NPe6 and the irradiation with laser can be focused on choriocapillaris itself only but do not directly affect the sensory retina to a substantial extent.

(4) The eye having received the intravenous injection of a dose of 25 mg/kg of NPe6 was subjected to the irradiation with the laser at 664 nm immediately after the intravenous injection of NPe6. The laser-irradiated parts of the eye so treated were subsequently observed under light microscope at the end of 1 hour after the laser irradiation. By this observation, At was found that the choroidal blood vessels, more particularly the choriocapillaris continued to have been obstructed, From these findings, it is considered that the obstruction of the blood vessels as achieved by the associated actions of the administration of Npe6 and the irradiation with laser can be maintained for a prolonged period directly after the laser irradiation.

(5) Comparisons under light microscope were made between the coagulated lesions of the choroidal blood vessels, which had been formed by the thermal actions of a conventional irradiation with an argon laser ray, and the coagulated lesions of the choroidal vessels, which had been formed by the administration of NPe6 and the subsequent irradiation with Laser ray according to the present invention, wherein the laser irradiation was made immediately after the administration of a dose of NPe6 of 25 mg/kg and the microscopic observations were done at the end of one week after the laser irradiation.

By these observations, it was found that the choroidal vessels were obstructed to a substantially same degree in the former case and the latter case, and that the damages incurred in the sensory retina were lighter in the latter case, that is, upon the administration of NPe6 associated with the subsequent irradiation with laser ray, than those in the former case, that is, upon the conventional photo-coagulation with the argon laser ray. This finding clearly shows that the action of the argon laser ray used in the conventional photo-coagulation is different from the action of the laser irradiation as associated with the administration of the photochemotherapeutic obstruent, NPe6 according to the present invention, and also suggests that the present invention makes it feasible to achieve a selective obstruction in such predetemined regions of the blood vessels, where an effective amount of NPe6 is presented there.

TEST EXAMPLE 2

Normal pigmented rabbits of a sort same as that employed in the above Test Example 1 were intravenously administered with a dose of NPe6 of 100 mg/kg at their eyes in the same manner as in Test Example 1 and were subsequently housed for one week under ordinary fluorescent tubes of the usual living environments without receiving any irradiation with the laser ray. The eyes of the rabbits so housed were then examined by observing the fluorescein angiography and the light microscopic views of the fundus of the eyes. It was then found that the so housed rabbits were able to retain the normal structures in the retina and choroid of their eyes, despite that they had received the administration of a maximum dosage of NPe6. This finding reveals that NPe6 is a photosensitive substance with a high safety, which does not adversely affect mammals when the mammals are kept under ordinary fluorescent lights of the usual living environments.

Next, some illustrative formulations of the obstruent composition according to this invention are given below.

EXAMPLE 1 OF FORMULATION

The following ingredients were mixed together in the proportions by weight as indicated below, to prepare a basal powder:

| | |
|---|---|
| Sucrose | 80.3 gramms |
| Tapioca starch | 13.2 gramms |
| Magnesium stearate | 4.4 gramms |

The basal powder so obtained was mixed well with an appropriate amount of NPe6 and the resulting mixture was shaped into tablets by a conventional tableting method, so that there were produced tablets each containing 100 mg of NPe6 as the active ingredient.

EXAMPLE 2 OF FORMULATION

In a volume of physiological saline were dissolved 200 mg of NPe6 to give an aqueous solution which contained NPe6 dissolved in the saline at a final NPe6 concentration of 20 mg per ml. The resulting solution was sterilized in a conventional manner to afford an injectable solution of NPe6, which is suitable for intravenous administration and also for intramuscular administration for the photochemotherapeutic purposes.

We claim:

1. A method for photochemotherapeutically obstructing neovascular vessels as foraged in a patient having the neovascular vessels, which comprises administering orally or parenterally to the patient an amount of a compound having the formula (I):

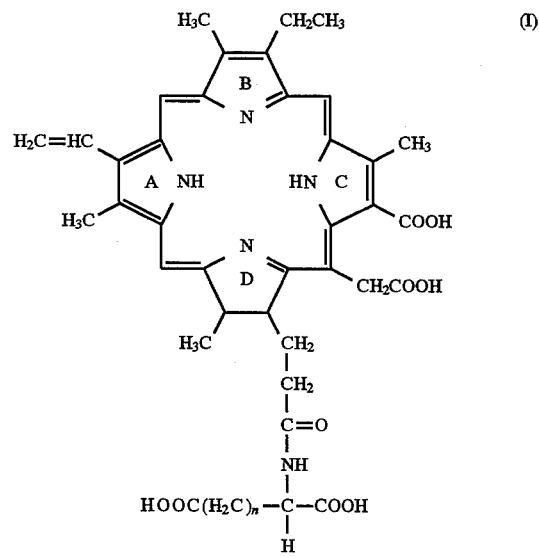

where n stands for an integer of 1 or 2, or a pharmaceutically acceptable salt thereof, allowing said compound administered to accumulate in the neovascular vessels to be obstructed after the administration of said compound to the patient, irradiating a part or all or some parts of the neovascular vessels to be obstructed, with a laser beam until the compound accumulated in the neovascular vessels has been elicited photochemically, terminating the irradiation of the laser beam, and then allowing the laser beam-irradiated part or parts of the neovascular vessels to be obstructed.

2. A method according to claim 1, which is applied to the photochemotherapeutical obstruction of the choroidal or retinal neovascularization.

* * * * *